US010059717B2

(12) United States Patent
Sim et al.

(10) Patent No.: US 10,059,717 B2
(45) Date of Patent: Aug. 28, 2018

(54) UREA COMPOUNDS CONTAINING 3,4-DIHYDROPYRIMIDO[4,5-D]PYRIMIDIN-2(1H)-ONE SKELETON AS PROTEIN KINASE INHIBITORS

(71) Applicant: KOREA INSTITUTE OF SCIENCE AND TECHNOLOGY, Seoul (KR)

(72) Inventors: Tae Bo Sim, Seoul (KR); Woo Young Hur, Seoul (KR); Ho Jong Yoon, Seoul (KR); Chi Man Song, Seoul (KR); Eun Hye Ju, Seoul (KR); Han na Cho, Seoul (KR); Hwan Geun Choi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/674,023

(22) Filed: Aug. 10, 2017

(65) Prior Publication Data
US 2018/0065970 A1    Mar. 8, 2018

(30) Foreign Application Priority Data

Aug. 10, 2016    (KR) .......................... 10-2016-0101545

(51) Int. Cl.
*C07D 487/04*    (2006.01)
*C07D 403/14*    (2006.01)
*C07D 401/14*    (2006.01)
*A61K 31/4985*    (2006.01)
*A61P 35/00*    (2006.01)
*A61P 35/02*    (2006.01)

(52) U.S. Cl.
CPC ......... *C07D 487/04* (2013.01); *C07D 401/14* (2013.01); *C07D 403/14* (2013.01)

(58) Field of Classification Search
CPC ... C07D 487/04; C07D 401/14; C07D 403/14
See application file for complete search history.

(56) References Cited

U.S. PATENT DOCUMENTS

2009/0099190 A1*    4/2009    Flynn ................... C07D 471/04
                                                                    514/249

FOREIGN PATENT DOCUMENTS

WO    WO 2015/011597 A1    1/2015

OTHER PUBLICATIONS

Choi et al., "A Type-II Kinase Inhibitor Capable of Inhibiting the T315I "Gatekeeper" Mutant of Bcr-Abl", Journal of Medicinal Chemistry 2010, vol. 53, No. 15, pp. 5439-5448.
Jain et al., "Phase II Study of the Oral MEK Inhibitor Selumetinib in Advanced Acute Myelogenous Leukemia: A University of Chicago Phase II Consortium Trial", Clin Cancer Res; Jan. 15, 2014, vol. 20, No. 2, pp. 490-498.
Johnson et al., "Molecular Pathways: Targeting NRAS in Melanoma and Acute Myelogenous Leukemia", Clin Cancer Res; Aug. 15, 2014, vol. 20, No. 16, pp. 4186-4192.
Luo et al., "STK33 kinase inhibitor BRD-8899 has no effect on KRAS-dependent cancer cell viability", PNAS, Feb. 21, 2012, vol. 109, No. 8, pp. 2860-2865. www.pnas.org/cgi/doi10.1073/pnas.1120589109.
Nonami et al., "Identification of novel therapeutic targets in acute leukemias with NRAS mutations using a pharmacologic approach", Blood, May 14, 2015, vol. 125, No. 20, pp. 3133-3143.

* cited by examiner

*Primary Examiner* — John M Mauro
(74) *Attorney, Agent, or Firm* — Birch, Stewart, Kolasch & Birch, LLP

(57) ABSTRACT

The present invention provides a pharmaceutical composition, as an effective ingredient, a urea compound having a protein kinase inhibitory activity and containing a 3,4-dihydropyrimido[4,5-d]pyrimidin-2(1H)-one skeleton, and a pharmaceutically acceptable salt thereof.

11 Claims, 1 Drawing Sheet

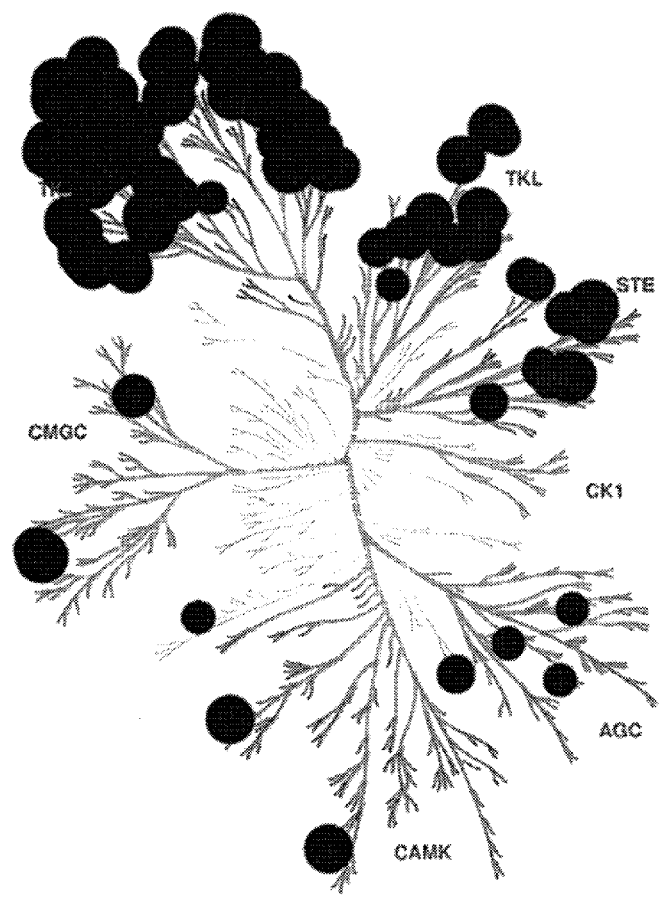

UREA COMPOUNDS CONTAINING 3,4-DIHYDROPYRIMIDO[4,5-D]PYRIMIDIN-2(1H)-ONE SKELETON AS PROTEIN KINASE INHIBITORS

CROSS-REFERENCE TO RELATED APPLICATION

This non-provisional application claims the benefit under 35 U.S.C. § 119(a) to Patent Application No. 10-2016-0101545, filed in the Republic of Korea on Aug. 10, 2016, all of which are hereby expressly incorporated by reference into the present application.

BACKGROUND

(a) Technical Field

The present disclosure relates to urea compounds having a protein kinase inhibitory activity and containing a 3,4-dihydropyrimido[4,5-d]pyrimidin-2(1H)-one skeleton, and pharmaceutical compositions comprising such compounds as active ingredients.

(b) Background Art

Protein kinases are enzymes that catalyze phosphorylation of the hydroxyl groups located on tyrosine, serine, and threonine residues of a protein and play an important role in growth factor signaling that leads to cellular growth, differentiation and proliferation.

In order to maintain homeostasis in a living body, in vivo signaling systems should be well balanced between their turn-ons and turn-offs. However, mutation or overexpression of a certain protein kinase disrupts a normal intracellular signaling system (predominantly into a state that an in vivo signaling is continued), thereby causing a variety of diseases, such as cancers, inflammation, metabolic diseases, and brain diseases. Representative protein kinases, which cause abnormal cell growth diseases, include Raf, KDR, Fms, Tie2, SAPK2a, Ret, Abl, Abl (T3151), ALK, Aurora A, Bmx, CDK/cyclinE, Kit, Src, EGFR, EphA1, FGFR3, FLT3, Fms, IGF-1R, IKKb, IR, Itk, JAK2, KDR, Met, mTOR, PDGFRa, Plk1, Ret, Syk, Tie2, TrtB, and the like. Thus, studies are underway to develop targeted anti-cancer drugs by developing compounds having a selective inhibitory activity against a specific kinase among several protein kinases.

On the other hand, acute myelogenous leukemia (AML) is one of the deadly blood diseases and is a disease where blood cells constantly proliferate with abnormal differentiation. 16% or more of patients with acute myelogenous leukemia (AML) have a point-mutated RAS (small G protein) protein, wherein among RAS isoforms, mutation of NRAS accounts for the majority (10% or more). For this reason, the NRAS G protein has been regarded as a promising drug target for the treatment of AML. When oncogenic RAS is mutated, RAS is continuously activated (gain-of-function), and various signaling systems downstream of RAS are activated to accelerate cancer cell growth.

Over the last 40 years, RAS point mutation species or key signaling molecules downstream of RAS have been proposed as targets. However, the complexity and compensation effects in the signaling systems of a mutant RAS have resulted in failure to lead to in vivo experiments and clinical trials. For example, selumetinib (AZD 6244) inhibiting MEK, a major molecule downstream of RAS, has not exhibited therapeutic effects in all three AML patients with a mutant NRAS gene in phase II. In addition, in an attempt to find targets, RNA interference screening was used to identify proteins (TBK1, STK33 and GATA2) which are genetically in a synthetic lethal relationship with mutation of KRAS. However, this also failed to achieve clinical therapeutic effects. In particular, in the case of STK33, it was proven through a cell-based pharmacologic screening at the preclinical stage that therapeutic strategies using mutation of KRAS and synthetic lethal principles cannot be established. Recently, a cell-based pharmacological screening was used to identify a compound (GNF 7) that selectively inhibits the signaling system of a mutant RAS, and its inhibitory effects in preclinical leukemia models have been observed. The action mechanism of the GNF 7 compound is to simultaneously inhibit both kinases, GCK and ACK1, which specifically contribute to cell growth downstream of the mutant RAS. This compound also exhibited its efficacy in cell samples from AML patients with actual NRAS mutants. Inhibitors for both kinases, GCK and ACK1, are known to be effective for the treatment of cancerous diseases caused by mutation of NRAS, such as melanoma, colorectal cancer, thyroid cancer, and various hematologic malignancies.

On the other hand, WO 2005-011597 (Patent Document 1) discloses an amide compound having 3,4-dihydropyrimido[4,5-d]pyrimidin-2(1H)-one as a mother nucleus structure, and discloses that the compound is effective for the treatment of diseases or symptoms caused by a kinase activity associated with Abl, BCR-Abl, and the like. However, the above-mentioned Patent Document 1 merely discloses that the amide compound is useful as a therapeutic agent for chronic myelogenous leukemia (CML), based on its BCR-Abl inhibitory activity.

CITATION LIST

Patent Literature (Patent Literature 1) WO 2005011597

Non-Patent Literature (Non-Patent Literature 1) Choi H G, Ren P, Adrian F, et al., A type-II kinase inhibitor capable of inhibiting the T3151 "gatekeeper" mutant of Bcr-Abl. J. Med. Chem., 2010; 53(15): 5439-5448

(Non-Patent Literature 2) Nonami, A.; Sattler, M.; Weisberg, E.; Liu, Q.; Zhang, J.; Patricelli, M. P.; Christie, A. L.; Saur, A. M.; Kohl, N. E.; Kung, A. L.; Yoon, H.; Sim, T.; Gray, N. S.; Griffin, J. D., Identification of novel therapeutic targets in acute leukemias with NRAS mutations using a pharmacologic approach. Blood 2015, 125 (20), 3133-43

(Non-Patent Literature 3) Luo T, Masson K, Jaffe J D, et al., STK33 kinase inhibitor BRD-8899 has no effect on KRASdependent cancer cell viability. Proc Natl Acad Sci USA, 2012; 109(8): 2860-2865

(Non-Patent Literature 4) Jain N, Curran E, lyengar N M, et al., Phase II study of the oral MEK inhibitor selumetinib in advanced acute myelogenous leukemia: a University of Chicago phase II consortium trial. Clin Cancer Res. 2014; 20(2): 490-498.

(Non-Patent Literature 5) Johnson, D. B.; Smalley, K. S.; Sosman, J. A., Molecular pathways: targeting NRAS in melanoma and acute myelogenous leukemia. Clin Cancer Res 2014, 20(16), 4186-92

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art.

In one aspect, the present invention provides a novel urea compound having a protein kinase inhibitory activity and containing a 3,4-dihydropyrimido[4,5-d]pyrimidin-2(1H)-one skeleton.

In another aspect, the present invention provides a pharmaceutical composition useful for the treatment, prevention and alleviation of cancerous diseases, the composition including, as an effective ingredient, a novel urea compound containing a 3,4-dihydropyrimido[4,5-d]pyrimidin-2(1H)-one skeleton, a pharmaceutically acceptable salt, hydrate, solvate or isomer thereof.

In a further aspect, the present invention provides a therapeutic agent for cancerous diseases caused by mutation of NRAS, the agent including, as an effective ingredient, a novel urea compound containing a 3,4-dihydropyrimido[4,5-d]pyrimidin-2(1H)-one skeleton, a pharmaceutically acceptable salt, hydrate, solvate or isomer thereof.

In order to solve the above-described problems, the present invention provides a urea compound containing a 3,4-dihydropyrimido[4,5-d]pyrimidin-2(1H)-one skeleton and represented by the following Formula 1, a pharmaceutically acceptable salt, hydrate, solvate or isomer thereof.

[Formula 1]

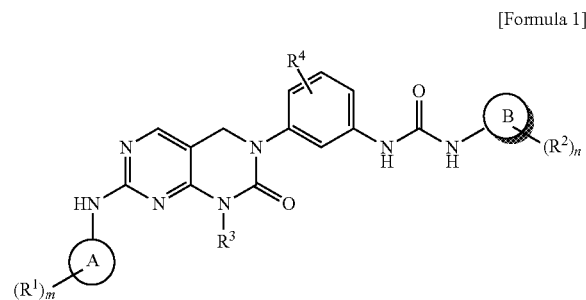

In the above Formula 1,

A and B each represent a $C_6$-$C_{15}$ aryl group, or a 5- to 14-membered heteroaryl group containing 1 to 4 hetero atoms selected from nitrogen (N), oxygen (O) and sulfur (S) atoms, $R^1$ and $R^2$ represent a halogen atom, an oxo group (=O), a $C_1$-$C_6$ alkyl group, a $C_1$-$C_6$ haloalkyl group, —O—($C_1$-$C_6$ alkyl), —O—($C_1$-$C_6$ haloalkyl), —C(O)—($C_1$-$C_6$ alkyl), —C(O)—O—($C_1$-$C_6$ alkyl), —O—C(O)—($C_1$-$C_6$ alkyl), —NR$^5$R$^6$, —C(O)—NR$^5$R$^6$, or —O—($C_1$-$C_6$ alkyl)-NR$^5$R$^6$, $R^3$ represents a hydrogen atom, a $C_1$-$C_6$ alkyl group, —O—($C_1$-$C_6$ alkyl), or —C(O)—($C_1$-$C_6$ alkyl), $R^4$ represents a hydrogen atom, a $C_1$-$C_6$ alkyl group, or —O—($C_1$-$C_6$ alkyl);

$R^5$ and $R^6$ each represent a hydrogen atom or a $C_1$-$C_6$ alkyl group, or $R^5$ and $R^6$ may be bonded to each other to form a 5- to 6-membered heterocyclic group including 1 to 2 hetero atoms selected from nitrogen (N) and oxygen (O) atoms, wherein the heterocyclic group may be optionally substituted by a hydroxyl group, $C_1$-$C_6$ alkyl, —($C_1$-$C_6$ hydroxyalkyl), —O—($C_1$-$C_6$ alkyl), —C(O)—($C_1$-$C_6$ alkyl), or —C(O)NH$_2$, m and n are an integer of 0 to 3.

The compounds according the present invention have an excellent ability to inhibit the activity of protein kinases such as ABL1, FGFR2, TAOK2/TAO1, EPHA5, EPHB2, EPHB3, RET, LYN B, EPHA2, FRK/PTK5, EPHA8, LCK, EPHB4, FYN, KHS/MAP4K5, DDR1, EPHA3, P38a/MAPK14, EPHA4, FMS, EPHB1, HCK, FGFR1, ABL2/ARG, EPHA6, c-Src, ACK1, FLT4NEGFR3, ERBB4/HER4, DDR2, KDRNEGFR2, LYN, ZAK/MLTK, YES/YES1, BLK, FGR, MLCK2/MYLK2, TAOK1, BMX/ETK, BTK, EPHA1, JAK1, P38b/MAPK11, TIE2/TEK, FLT1NEGFR1, TXK, SRMS, RAF1, SIK1, MLK3/MAP3K11, PEAK1, TRKA, EPHA7, GLK/MAP4K3, MLK2/MAP3K10, TEC, CSK, TRKC, FES/FPS, SIK2, FGFR3, BRK, YSK4/MAP3K19, ARAF, PDGFRb, TNK1, GCK/MAP4K2, PDGFRa, TNIK, TAK1, ERBB2/HER2, LIMK1, HIPK4, FER, EGFR, JAK2, HPK1/MAP4K1, TRKB, RIPK3, LOK/STK10, LIMK2, MLK1/MAP3K9, BRAF, MEKK3, MEK5, STK32B/YANK2, FGFR4, MEKK2, SLK/STK2, FLT3, PKAcg, TAOK3/JIK, TYRO3/SKY, SIK3, IR, LRRK2, PYK2, NEK11, p70S6K/RPS6KB1, and LATS2. Thus, these compounds can be used for the treatment, prevention and alleviation of cancerous diseases caused by abnormal cell growth.

The cancerous diseases which can be treated, prevented and alleviated by the treatment of the compounds according to the present invention may include gastric cancer, lung cancer, liver cancer, colorectal cancer, small bowel cancer, pancreatic cancer, brain cancer, bone cancer, melanoma, breast cancer, sclerosing adenosis, uterine cancer, cervical cancer, head and neck cancer, esophageal cancer, thyroid carcinoma, parathyroid carcinoma, renal cancer, sarcoma, prostate cancer, urethral cancer, bladder cancer, hematologic malignancy (Including leukemia, multiple myeloma and myelodysplastic syndrome), lymphoma (including Hodgkin's disease and non-Hodgkin lymphoma), psoriasis, or fibroadenoma, or the like.

In particular, due to their excellent inhibitory activity against both kinases, GCK and ACK1, the compounds according to the present invention are effective for the treatment of cancerous diseases caused by mutation of NRAS, such as melanoma, colorectal cancer, thyroid cancer, and acute myelogenous leukemia (AML).

Other aspects and preferred embodiments of the invention are discussed infra.

The above and other features of the invention are discussed infra.

BRIEF DESCRIPTION OF THE DRAWINGS

The above and other features of the present invention will now be described in detail with reference to certain exemplary embodiments thereof illustrated in the accompanying drawings which are given herein below by way of illustration only, and thus are not limitative of the present invention, and wherein:

The FIGURE is a schematic representation of measurement results for the inhibitory efficacy of the compound of the present invention against 100 types of kinases. In the FIGURE, the inhibitory efficacy for protein kinase proliferation is exhibited by the size of circles.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the FIGURE, reference numbers refer to the same or equivalent parts of the present invention throughout the several FIGURES of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention features a urea compound containing a 3,4-dihydropyrimido[4,5-d]pyrimidin-2(1H)-one skeleton and represented by the following Formula 1.

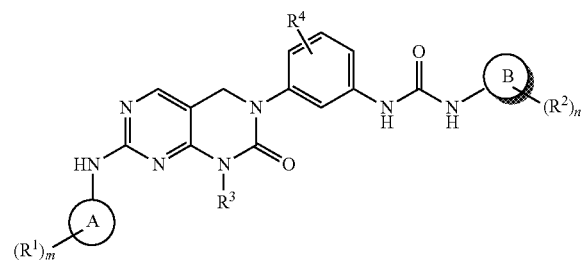

[Formula 1]

In the above Formula 1,

A and B each represent a $C_6$-$C_{15}$ aryl group, or a 5- to 14-membered heteroaryl group including 1 to 4 hetero atoms selected from nitrogen (N), oxygen (O) and sulfur (S) atoms, $R^1$ and $R^2$ represent a halogen atom, an oxo group (=O), a $C_1$-$C_6$ alkyl group, a $C_1$-$C_6$ haloalkyl group, —O—($C_1$-$C_6$ alkyl), —O—($C_1$-$C_6$ haloalkyl), —C(O)—($C_1$-$C_6$ alkyl), —C(O)—O—($C_1$-$C_6$ alkyl), —O—C(O)—($C_1$-$C_6$ alkyl), —NR$^5$R$^6$, —C(O)—NR$^5$R$^6$, or —O—($C_1$-$C_6$ alkyl)-NR$^5$R$^6$, $R^3$ represents a hydrogen atom, a $C_1$-$C_6$ alkyl group, —O—($C_1$-$C_6$ alkyl), or —C(O)—($C_1$-$C_6$ alkyl), $R^4$ represents a hydrogen atom, a $C_1$-$C_6$ alkyl group, or —O—($C_1$-$C_6$ alkyl);

$R^5$ and $R^6$ each represent a hydrogen atom or a $C_1$-$C_6$ alkyl group, or $R^5$ and $R^6$ may be bonded to each other to form a 5- to 6-membered heterocyclic group including 1 to 2 hetero atoms selected from nitrogen (N) and oxygen (O) atoms, wherein the heterocyclic group may be optionally substituted by a hydroxyl group, a $C_1$-$C_6$ alkyl group, —($C_1$-$C_6$ hydroxyalkyl), —O—($C_1$-$C_6$ alkyl), —C(O)—($C_1$-$C_6$ alkyl), or —C(O)NH$_2$, m and n are an integer of 0 to 3.

The compounds according to the present invention include pharmaceutically acceptable salts of the compound represented by the above Formula 1. The pharmaceutically acceptable salts should be low in toxicity to a human body and should not adversely affect the biological activities and physicochemical properties of its parent compound. Pharmaceutically acceptable salts include acid addition salts of the basic compound of Formula 1 with a pharmaceutically acceptable free acid, alkali metal salts (such as sodium salts), alkaline earth metal salts (such as calcium salts), and organic base addition salts of the carboxylic acid of Formula 1 with an organic base and amino acid addition salts. The free acid that can be used to prepare pharmaceutically acceptable salts may be divided into an inorganic acid and an organic acid. For the inorganic acid, hydrochloric acid, sulfuric acid, nitric acid, phosphoric acid, perchloric acid, bromic acid, and the like may be used. For the organic acid, acetic acid, methanesulfonic acid, ethanesulfonic acid, p-toluenesulfonic acid, trifluoroacetic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like may be used. An organic base that can be used to prepare organic base addition salts includes tris(hydroxymethyl)methylamine, dicyclohexylamine, and the like. An amino acid that can be used to prepare amino acid addition salts is a natural amino acid such as alanine and glycine.

The compounds according to the present invention also include hydrates or solvates of the compound represented by the above Formula 1. The hydrates or solvates may be prepared by conventional methods, examples of which may include dissolving the basic compound of the above Formula 1 in a solvent such as water, methanol, ethanol, acetone, or 1,4-dioxane, then adding a free acid or base, followed by crystallization or recrystallization.

The compound represented by the above Formula 1 may have one or more centers of asymmetry, and in the case of this compound, enantiomers or diastereomers may exist. Accordingly, the compounds of the present invention include their respective isomers or a mixture thereof. Different isomers may be separated or resolved by conventional methods, or any desired isomer may be obtained by conventional synthetic methods or by stereospecific or asymmetric synthesis.

The compounds of the present invention include radioactive derivatives of the compound represented by the above Formula 1, and these radioactive compounds are useful in the field of biotrepy.

The substituents used to define the compound represented by the above Formula 1 will be described in more detail as follows.

As used herein, the term "halo" or "halogen atom" is used interchangeably and refers to chloro, fluoro, bromo, or iodo.

As used herein, the term "alkyl" refers to a straight, branched or cyclic aliphatic saturated hydrocarbon group having 1 to 10 carbon atoms, preferably 1 to 6 carbon atoms, more preferably 1 to 4 carbon atoms. Specific examples of such an alkyl group may include a methyl group, an ethyl group, a normal propyl group, an isopropyl group, a cyclopropyl group, a cyclopropylmethyl group, a normal butyl group, an isobutyl group, a tert-butyl group, a cyclobutyl group, a normal pentyl group, an isopentyl group, a neopentyl group, a tert-pentyl group, a cyclopentyl group, a normal hexyl group, an isohexyl group, a cyclohexyl group, a normal heptyl group, a normal octyl group, and the like.

As used herein, the term "haloalkyl group" includes all straight or branched carbon chains having 1 to 13 halogen atoms such as fluoro, chloro, bromo and iodo, and having 1 to 10 carbon atoms. Specific examples of such a haloalkyl group may include a fluoromethyl group, a trifluoromethyl group, a 1,2-dichloroethyl group, a 1,1-dichloroethyl group, a pentafluoroethyl group, and the like.

As used herein, the term "alkoxy group" refers to —O—($C_1$-$C_{10}$ alkyl), and its specific examples may include a methoxy group, an ethoxy group, a propoxy group, a tert-butoxy group and a cyclohexyloxy group.

As used herein, the term "heterocyclic group" refers to a 5-membered or 6-membered aliphatic ring group including 1 to 2 hetero atoms selected from nitrogen (N) and oxygen (O) atoms. Specific examples of such a heterocyclic group may include a tetrahydrofuranyl group, a 2,3-dihydrofuranyl group, a 2,5-dihydrofuranyl group, a pyrrolidinyl group, a 2,3-dihydropyrrolidinyl group, a 2,5-dihydropyrrolidinyl group, a tetrahydro-2H-pyranyl group, a 3,4-dihydro-2H-pyranyl group, a 4H-pyranyl group, a piperidinyl group, a 1,2,3,4-tetrahydropyridinyl group, a 1,4-dihydropyridinyl group, a piperazinyl group, an N-protected piperazinyl, a morpholino group, and the like. Also, the heterocyclic group may be optionally substituted by —OH, a $C_1$-$C_{10}$ alkyl group, —($C_1$-$C_{10}$ hydroxylalkyl), —O—($C_1$-$C_{10}$ alkyl), —C(O)—($C_1$-$C_{10}$ alkyl), or —C(O)$NH_2$.

As used herein, the term "aryl" refers to a monocyclic, bicyclic or tricyclic aromatic hydrocarbon group having 6 to 15 carbon atoms. Specific examples of such an aryl group may include a phenyl group, a naphthyl group, and the like.

As used herein, the term "heteroaryl" refers to a 5- to 14-membered monocyclic, bicyclic or tricyclic aromatic ring group including 1 to 4 hetero atoms selected from nitrogen (N), oxygen (O) and sulfur (S) atoms. Such a heteroaryl may include a thiophenyl group, a pyrrolyl group, a pyrazolyl group, an imidazolyl group, a thiazolyl group, an isothiazolyl group, a pyridinyl group, a pyrazinyl group, a pyridazinyl group, a pyrimidinyl group, an indolyl group, an isoindolyl group, an indazolyl group, a benzimidazolyl group, a benzothiazolyl group, a benzisothiazolyl group, a quinolinyl group, an isoquinolinyl group, a phthalazinyl group, a quinazolinyl group, and the like.

In the compound represented by the above Formula 1, the preferred compound is a compound wherein A represents a phenyl group, a pyridinyl group or a pyrazole group, B represents a phenyl group, $R^1$ represents a $C_1$-$C_6$ alkyl group, —C(O)—($C_1$-$C_6$ alkyl), —$NR^5R^6$, —C(O)—$NR^5R^6$, $R^2$ represents a halogen group, a $C_1$-$C_6$ alkyl group, a $C_1$-$C_6$ haloalkyl group, —O—($C_1$-$C_6$ alkyl), or —O—($C_1$-$C_6$ haloalkyl), $R^3$ represents a hydrogen atom or a $C_1$-$C_6$ alkyl group, $R^4$ represents a hydrogen atom or a $C_1$-$C_6$ alkyl group, $R^5$ and $R^6$ each represent a hydrogen atom or a $C_1$-$C_6$ alkyl group, or $R^5$ and $R^6$ may be bonded to each other to form a heterocyclic group selected from piperidine, piperazinyl and morpholyl, wherein the heterocyclic group may be optionally substituted by a $C_1$-$C_6$ alkyl group, —C(O)—($C_1$-$C_6$ alkyl) or —C(O)$NH_2$, and m and n represent an integer of 0, 1 or 2.

In the compound represented by the above Formula 1, the more preferred compound is the one wherein $R^1$ represents a methyl group, an ethyl group, a propyl group, a piperidinyl group, a 4-(carbamoyl)piperidinyl group, a piperazinyl group, a 4-(ethyl)piperazinyl group, a 4-(acetyl)piperazinyl group, a 4-(carbamoyl)piperazinyl group, —C(O)$NHCH_3$, —C(O)NH-cyclopropane, —C(O)-piperidine, —C(O)-piperazine, or —C(O)-4-(ethyl)piperazine, and m represents an integer of 0, 1 or 2.

In the compound represented by the above Formula 1, the more preferred compound is the one wherein $R^2$ represents chloro, fluoro, a methyl group, a methoxy group, an ethyl group, an ethoxy group, a trifluoromethyl group, or a trifluoromethoxy group, and m represents an integer of 0, 1 or 2.

Specific examples of the compound represented by the above Formula 1 are as follows:

1-(2-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 1);

1-(4-methyl-3-(1-methyl-7-((6-methylpyridin-3-yl)amino)-2-oxo-1,4-dihydropyrimido[4,5-d]pyrimidin-3(2H)-yl)phenyl)-3-phenylurea (Compound No. 2);

1-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-(trifluoromethoxy)phenyl)urea (Compound No. 3);

1-(4-methyl-3-(1-methyl-7-((6-methyl pyridin-3-yl)amino)-2-oxo-1,4-dihydropyrimido[4,5-d]pyrimidin-3(2H)-yl)phenyl)-3-(2-(trifluoromethyl)phenyl)urea (Compound No. 4);

1-(4-methyl-3-(1-methyl-7-((6-methylpyridin-3-yl)amino)-2-oxo-1,4-dihydropyrimido[4,5-d]pyrimidin-3(2H)-yl)phenyl)-3-(o-tolyl)urea (Compound No. 5);

1-(2,3-dichlorophenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 6);

1-(4-methyl-3-(1-methyl-7-((6-methylpyridin-3-yl)amino)-2-oxo-1,4-dihydropyrimido[4,5-d]pyrimidin-3(2H)-yl)phenyl)-3-(3-(trifluoromethyl)phenyl)urea (Compound No. 7);

1-(3-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 8);

1-(4-chloro-3-(trifluoromethyl)phenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 9);

1-(4-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 10);

1-(3-(7-((4-(4-ethylpiperazin-1-yl)phenyl)amino)-1-methyl-2-oxo-1,4-dihydropyrimido[4,5-d]pyrimidin-3(2H)-yl)-4-methylphenyl)-3-(2-methoxyphenyl)urea (Compound No. 11);

1-(2-methoxyphenyl)-3-(4-methyl-3-(1-methyl-7-((1-methyl-1H-pyrazol-4-yl)amino)-2-oxo-1,4-dihydropyrimido[4,5-d]pyrimidin-3(2H)-yl)phenyl)urea (Compound No. 12);

1-(3-(7-((6-(4-acetylpiperazin-1-yl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea (Compound No. 13);

1-(3-(7-((6-(4-ethylpiperazin-1-carbonyl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea (Compound No. 14);

5-((6-(5-(3-(2-methoxyphenyl)ureido)-2-methylphenyl)-8-methyl-7-oxo-5,6,7,8-tetrahydropyrimido[4,5-d]pyrimidin-2-yl)amino-N-methylpicolinamide (Compound No. 15);

N-cyclopropyl-5-((6-(5-(3-(2-methoxyphenyl)ureido)-2-methylphenyl)-8-methyl-7-oxo-5,6,7,8-tetrahydropyrimido[4,5-d]pyrimidin-2-yl)amino)picolinamide (Compound No. 16);

1-(3-(7-((6-(4-ethylpiperazin-1-yl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea (Compound No. 17);

1-(5-((6-(5-(3-(2-methoxyphenyl)ureido)-2-methylphenyl)-8-methyl-7-oxo-5,6,7,8-tetrahydropyrimido[4,5-d]pyrimidin-2-yl)amino)pyridin-2-yl)piperidin-4-carboxamide (Compound No. 18).

On the other hand, the present invention includes a pharmaceutical composition including, as an effective ingredient, the compound represented by the above Formula 1, or a pharmaceutically acceptable salt, solvate or hydrate thereof.

Pharmaceutical compositions according the present invention have an excellent ability to inhibit the activity of protein kinases. Specific examples of the protein kinases may include ABL1, FGFR2, TAOK2/TAO1, EPHA5, EPHB2, EPHB3, RET, LYN B, EPHA2, FRK/PTK5, EPHA8, LCK, EPHB4, FYN, KHS/MAP4K5, DDR1, EPHA3, P38a/MAPK14, EPHA4, FMS, EPHB1, HCK, FGFR1, ABL2/ARG, EPHA6, c-Src, ACK1, FLT4NEGFR3, ERBB4/HER4, DDR2, KDRNEGFR2, LYN, ZAK/MLTK, YES/YES1, BLK, FGR, MLCK2/MYLK2, TAOK1, BMX/ETK, BTK, EPHA1, JAK1, P38b/MAPK11, TIE2/TEK, FLT1NEGFR1, TXK, SRMS, RAF1, SIK1, MLK3/MAP3K11, PEAK1, TRKA, EPHA7, GLK/MAP4K3, MLK2/MAP3K10, TEC, CSK, TRKC, FES/FPS, SIK2, FGFR3, BRK, YSK4/MAP3K19, ARAF, PDGFRb, TNK1, GCK/MAP4K2, PDGFRa, TNIK, TAK1, ERBB2/HER2, LIMK1, HIPK4, FER, EGFR, JAK2, HPK1/MAP4K1, TRKB, RIPK3, LOK/STK10, LIMK2, MLK1/MAP3K9, BRAF, MEKK3, MEK5, STK32B/YANK2, FGFR4, MEKK2, SLK/STK2, FLT3, PKAcg, TAOK3/JIK, TYRO3/SKY, SIK3, IR, LRRK2, PYK2, NEK11, p70S6K/RPS6KB1, LATS2, and the like.

Thus, the pharmaceutical compositions of the present invention can be used for the treatment, prevention and alleviation of cancerous diseases caused by abnormal cell growth. The cancerous diseases which can be treated, prevented and alleviated by the treatment of the pharmaceutical compositions of the present invention may include gastric cancer, lung cancer, liver cancer, colorectal cancer, small bowel cancer, pancreatic cancer, brain cancer, bone cancer, melanoma, breast cancer, sclerosing adenosis, uterine cancer, cervical cancer, head and neck cancer, esophageal cancer, thyroid carcinoma, parathyroid carcinoma, renal cancer, sarcoma, prostate cancer, urethral cancer, bladder cancer, hematologic malignancy (Including leukemia, multiple myeloma and myelodysplastic syndrome), lymphoma (including Hodgkin's disease and non-Hodgkin lymphoma), psoriasis, or fibroadenoma, or the like.

In particular, since the pharmaceutical compositions of the present invention have an inhibitory activity against both kinases, GCK and ACK1, it is appreciated that they are effective for the treatment of cancerous diseases caused by mutation of NRAS, such as melanoma, colorectal cancer, thyroid cancer, and various hematologic malignancies. In addition, the compound represented by the above Formula 1 is particularly effective as a therapeutic agent for acute myelogenous leukemia (AML), since it exhibits a proliferation inhibitory activity for the NRAS mutant cell line (OCI-AML3) while not for the NRAS-wild type AML cell line.

The pharmaceutical compositions of the present invention include the compound represented by the above Formula 1, or a pharmaceutically acceptable salt, solvate, or hydrate thereof as an active ingredient, and to this, a conventional non-toxic pharmaceutically acceptable carrier, an adjuvant, an excipient, and the like may be added to formulate preparations which are customary in the pharmaceutical field, for example preparations for oral administration such as tablets, capsules, troches, liquids and suspensions, or preparations for parenteral administration.

Excipients that can be used in the pharmaceutical compositions of the present invention may include sweeteners, binders, solubilizers, solubilizing aids, wetting agents, emulsifiers, isotonic agents, adsorbents, disintegrants, antioxidants, preservatives, lubricants, fillers, fragrances, and the like. Examples may include lactose, dextrose, sucrose, mannitol, sorbitol, cellulose, glycine, silica, talc, stearic acid, stearin, magnesium stearate, magnesium aluminum silicate, starch, gelatin, tragacanth gum, alginic acid, sodium alginate, methylcellulose, sodium carboxylmethylcellulose, agar, water, ethanol, polyethyleneglycol, polyvinylpyrrolidone, sodium chloride, calcium chloride, orange essence, strawberry essence, vanilla flavor, and the like.

Doses for humans of the compounds according to the present invention may vary depending on a patient's age, weight, sex, dosage form, health condition, and severity of disease. Based on an adult patient weighing 70 kg, the doses are generally 0.01 to 1,000 mg/day, and depending on the judgment of a doctor or a pharmacist, may be administered once a day or divided into multiple doses at a predetermined interval.

The present invention will now be described in more detail with reference to the following examples, formulation examples and test examples. However, the following examples, formulation examples and test examples are given merely to illustrate the present invention and are not intended to limit the scope of the invention thereto.

EXAMPLES

The following examples illustrate the invention and are not intended to limit the same.

Representative Synthetic Example 1

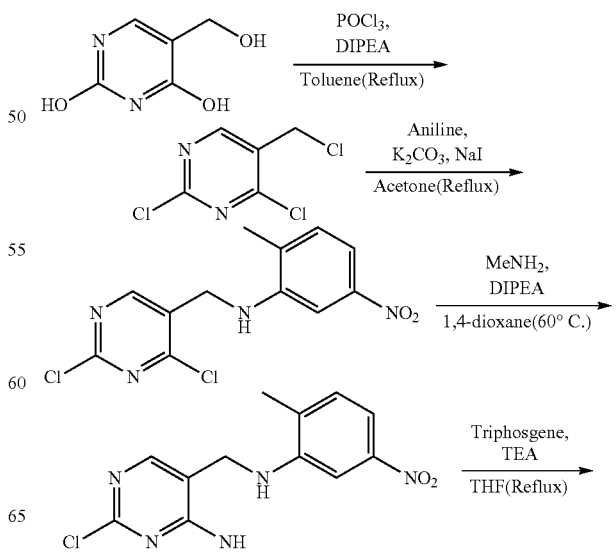

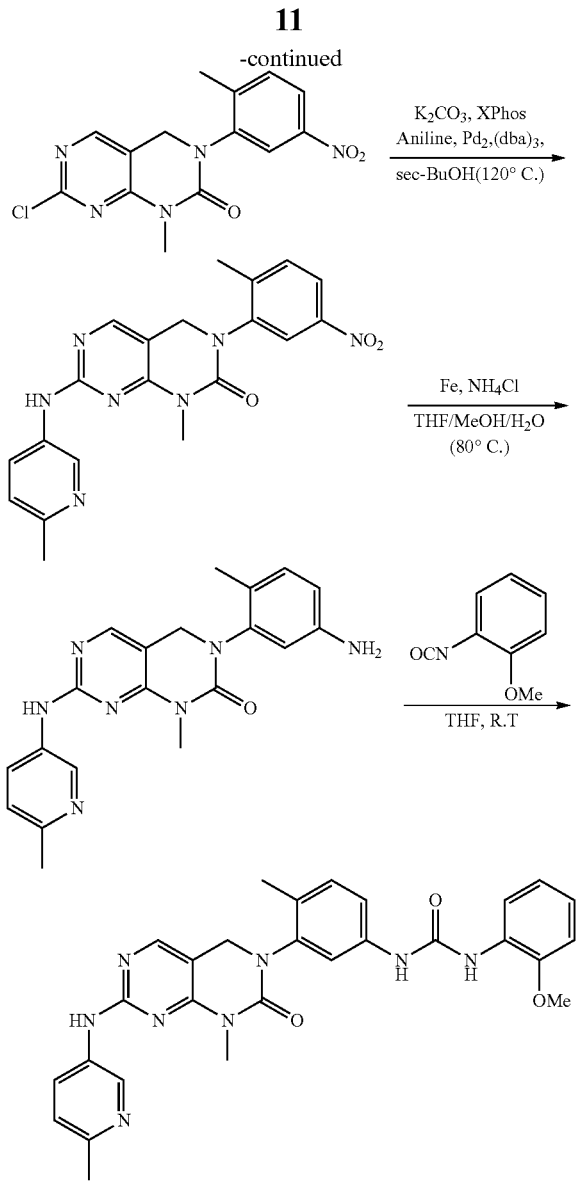

Step 1-1: 2,4-Dichloro-5-(chloromethyl)pyrimidine 5-(Hydroxymethyl)pyrimidin-2,4-diol (3 g, 21.1 mmol) and diisopropylethylamine (11 mL, 63.3 mmol) were added to toluene (8.4 mL), and then nitrogen gas was injected for 5 minutes to remove any gas contained in the mixed solution. Then, the reaction vessel was placed in an ice-water bath at 0° C., POCl$_3$ (9.8 mL, 105.5 mmol) was added, then the reaction vessel was transferred into an oil bath heated to 110° C., and stirred for 1 hour. Then, when the reaction was completed, the reaction mixture was cooled to room temperature and purified by column chromatography to obtain the desired compound (3.20 g, 76.7%) as a transparent liquid.

$^1$H NMR (400 MHz, CDCl$_3$) δ 8.66 (s, 1H), 4.64 (s, 2H).

Step 1-2: N-((2,4-dichloropyrimidin-5-yl) methyl)-2-methyl-5-nitroaniline 2,4-Dichloro-5-(chloromethyl)pyrimidine (2.4 g, 12.2 mmol) and 2-methyl-5-nitroaniline (1.48 g, 9.76 mmol) were dissolved in acetone (12 mL), then sodium iodide (2.2 g, 14.6 mmol) and potassium carbonate (2.5 g, 18.3 mmol) were added, and the mixture was stirred at 50° C. for 24 hours. When the reaction was completed, the mixture was cooled to room temperature and filtered using a celite pad. The filtrate was extracted with dichloromethane and water. The combined organic layers were dried over anhydrous magnesium sulfate and concentrated. The residue was purified by column chromatography to obtain the desired compound (2.83 g, 74.3%) as a yellow solid.

$^1$H NMR (400 MHz, DMSO-d$_6$) δ 8.66 (s, 1H), 7.42 (dd, J=2 Hz, J=8 Hz, 1H), 7.26 (d, J=8 Hz, 1H), 7.16 (d, J=2.4 Hz, 1H), 6.23 (t, J=5.6 Hz, 1H), 4.50 (d, J=5.6 Hz, 2H), 2.25 (s, 3H).

Step 1-3: 2-Chloro-N-methyl-5-(((2-methyl-5-nitrophenyl)amino)methyl)pyrimidin-4-amine N-((2,4-dichloropyrimidin-5-yl)methyl)-2-methyl-5-nitroaniline (2.83 g, 9.04 mmol) was dissolved in 1,4-dioxane. A methylamine/methanol mixture (4.52 mL, 18.1 mmol) and diisopropylethylamine (4.7 mL, 27.1 mmol) were added at a concentration of 2 M and the mixture was stirred at 60° C. for 1 hour and 30 minutes. When the reaction was completed, the mixture was cooled to room temperature and extracted with dichloromethane and water. The combined organic layers were dried over anhydrous magnesium sulfate and concentrated. The residue was purified by column chromatography to obtain the desired compound (2.15 g, 77.3%).

$^1$H NMR (400 MHz, DMSO-d$_6$) δ 7.90 (s, 1H), 7.53 (d, J=4.4 Hz, 1H), 7.39 (dd, J=2 Hz, J=8 Hz, 1H), 7.23 (d, J=8 Hz, 1H), 7.18 (d, J=2 Hz, 1H), 6.00 (t, J=5.6 Hz, 1H), 4.21 (d, J=5.6 Hz, 2H), 2.89 (d, J=4.4 Hz, 3H), 2.22 (s, 3H).

Step 1-4: 7-Chloro-1-methyl-3-(2-methyl-5-nitrophenyl)-3,4-dihydropyrimido[4,5-d]pyrimidin-2(1H)-One 2-Chloro-N-methyl-5-(((2-methyl-5-nitrophenyl)amino)methyl)pyrimidin-4-amine (5.12 g, 16.6 mmol) was dissolved in THF (50 mL), the reaction vessel was placed in an ice-water bath at 0° C., and stirred. Triphosgene (2.5 g, 8.2 mmol) was added, triethylamine (11.6 mL, 83 mmol) was added slowly, then the reaction vessel was transferred into an oil bath heated to 70° C., and stirred for 1 hour. When the reaction was completed, the reaction mixture was cooled to room temperature and extracted with dichloromethane and water. The combined organic layers were dried over anhydrous magnesium sulfate and concentrated. The residue was purified by column chromatography to obtain the desired compound (3.46 g, 62.5%) as a white solid.

$^1$H NMR (400 MHz, DMSO-d$_6$) δ 8.35 (d, J=2.4 Hz, 1H), 8.31 (s, 1H), 8.14 (dd, J=2.8 Hz, J=8.8 Hz, 1H), 7.62 (d, J=8.4 Hz, 1H), 4.94 (d, J=15.2 Hz, 1H), 4.65 (d, J=15.2 Hz, 1H), 3.28 (s, 3H), 2.27 (s, 3H).

Step 1-5: 1-Methyl-3-(2-methyl-5-nitrophenyl)-7-((6-methylpyridin-3-yl)amino)-3,4-dihydropyrimido[4,5-d]pyrimidin-2 (1H)-one 7-Chloro-1-methyl-3-(2-methyl-5-nitrophenyl)-3,4-dihydropyrimido[4,5-d]pyrimidin-2 (1H)-one (1.1 g, 3.3 mmol) was dissolved in 2-butanol (16.5 mL). 6-methylpyridine-3-amine (256.9 mg, 3.3 mmol) and potassium carbonate (2.2 g, 6.6 mmol) were added, the reaction vessel was transferred into an oil bath heated to 110° C., Pd$_2$(dba)$_3$ (604.3 mg, 0.66 mmol) and Xphos (314.6 mg, 0.66 mmol) were added, and the mixture was stirred for 90 minutes. When the reaction was completed, the reaction mixture was filtered using a celite pad and concentrated. The residue was purified by MPLC to obtain the desired compound (863.8 mg, 64.6%) as a yellow solid.

$^1$H NMR (400 MHz, DMSO-$d_6$) δ 9.66 (s, 1H), 8.79 (d, J=2.4 Hz, 1H), 8.34 (d, J=2.4 Hz), 8.14 (m, 2H), 8.05 (dd, J=2.8 Hz, J=8.4 Hz, 1H), 7.63 (d, J=8.8 Hz, 1H), 7.18 (d, J=8.4 Hz, 1H), 4.87 (d, J=13.6 Hz, 1H), 4.51 (d, J=13.6 Hz, 1H), 3.32 (s, 3H), 2.41 (s, 3H), 2.28 (s, 3H).

Step 1-6: 3-(5-Amino-2-methylphenyl)-1-methyl-7-((6-methylpyridin-3-yl)amino)-3,4-dihydropyrimido[4,5-d]pyrimidin-2(1H)-one 1-Methyl-3-(2-methyl-5-nitrophenyl)-7-((6-methylpyridin-3-yl)amino)-3,4-dihydropyrimido[4,5-d]pyrimidin-2(1H)-one (215.2 mg, 0.53 mmol) and ammonium chloride (567 mg, 10.6 mmol) were added to a mixed solution of THF/methanol/water (4:2:1, 17.5 mL), then iron powder (296 mg, 5.3 mmol) was added, and stirred at 80° C. for 2 hours. When the reaction was completed, the reaction mixture was cooled to room temperature and filtered using a celite pad. The filtrate was extracted with dichloromethane and water. The combined organic layers were dried over anhydrous magnesium sulfate and concentrated to obtain the desired compound (189.5 mg, 95.2%) as a pale yellow solid.

$^1$H NMR (400 MHz, DMSO-$d_6$) δ 9.60 (s, 1H), 8.78 (s, 1H), 8.12 (s, 1H), 8.04 (dd, J=2.8 Hz, J=8.4 Hz, 1H), 7.16 (d, J=8.4 Hz, 1H), 6.92 (d, J=8.8 Hz, 1H), 6.46 (m, 2H), 4.99 (s, 2H), 4.60 (d, J=14.4 Hz, 1H), 4.42 (d, J=14.4 Hz, 1H), 3.30 (s, 3H), 2.40 (s, 3H), 1.95 (s, 3H).

Step 1-7: 1-(2-Methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 1)

3-(5-Amino-2-methylphenyl)-1-methyl-7-((6-methylpyridin-3-yl)amino)-3,4-dihydropyrimido[4,5-d]pyrimidin-2(1H)-one (40 mg, 0.11 mmol) was dissolved in THF (2.2 mL), 2-methoxyphenyl isocyanate (0.02 mL, 0.14 mmol) was added, and the mixture was stirred at room temperature. After 1 hour, when the reaction was completed, the reaction mixture was extracted with dichloromethane and water, and the combined organic layers were dried over anhydrous magnesium sulfate and concentrated. The residue was purified by column chromatography to obtain the desired compound (25.3 mg, 43.8%) as a white solid.

Based on the method of Representative Synthesis Example 1, the compounds represented by Compound Nos. 1 to 10 were synthesized.

Compound No. 1. Synthesis of 1-(2-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea

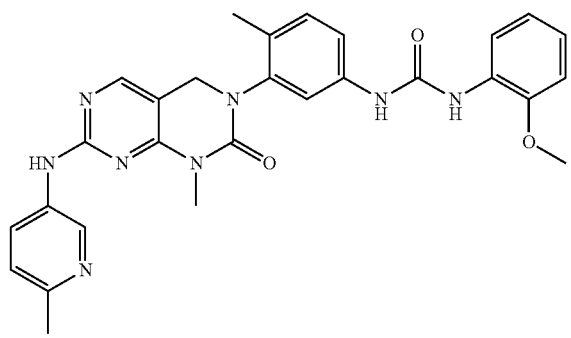

$^1$H NMR (400 MHz, DMSO-$d_6$) δ 9.63 (s, 1H), 9.36 (s, 1H), 8.80 (d, J=2.4 Hz, 1H), 8.23 (s, 1H), 8.13 (s, 1H), 8.12 (d, J=1.6 Hz, 1H), 8.06 (dd, J=2.4 Hz, J=8 Hz, 1H), 7.56 (d, J=1.6 Hz, 1H), 7.20 (m, 3H), 7.00 (dd, J=1.2 Hz, J=8.8 Hz, 1H), 6.93 (m, 2H), 4.70 (d, J=14 Hz, 1H), 4.48 (d, J=14.4 Hz, 1H), 3.87 (s, 3H), 3.33 (s, 3H), 2.40 (s, 3H), 2.08 (s, 3H).

Compound No. 2. Synthesis of 1-(4-methyl-3-(1-methyl-7-((6-methylpyridin-3-yl)amino)-2-oxo-1,4-dihydropyrimido[4,5-d]pyrimidin-3(2H)-yl)phenyl)-3-phenylurea

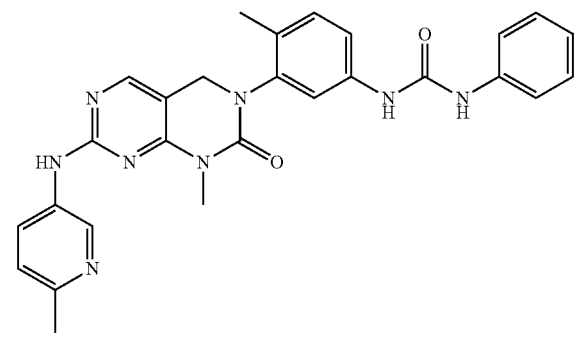 [SMILES: Cc1ccc(Nc2ncc3c(n2)N(C)C(=O)N(c2cc(NC(=O)Nc4ccccc4)ccc2C)C3)cn1]

$^1$H NMR (400 MHz, DMSO-$d_6$) δ 9.64 (s, 1H), 8.79 (d, J=2.4 Hz, 1H), 8.69 (d, J=2.8 Hz, 2H), 8.15 (s, 1H), 8.04 (dd, J=2.4 Hz, J=8 Hz, 1H), 7.53 (d, J=2 Hz, 1H), 7.45 (d, J=7.6 Hz, 2H), 7.23 (m, 5H), 6.96 (t, J=7.2 Hz, 1H), 4.70 (d, J=14 Hz, 1H), 4.49 (d, J=14 Hz, 1H), 2.40 (s, 3H), 2.08 (s, 3H).

Compound No. 3. Synthesis of 1-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-(trifluoromethoxy)phenyl)urea

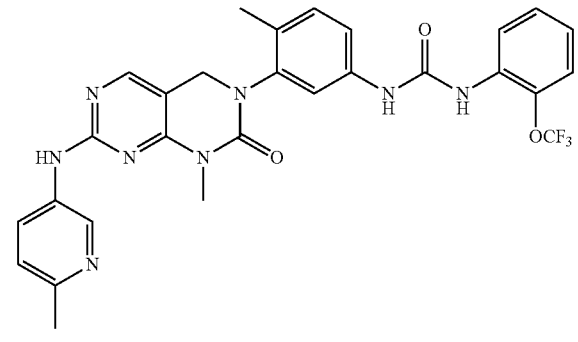 [SMILES: Cc1ccc(Nc2ncc3c(n2)N(C)C(=O)N(c2cc(NC(=O)Nc4ccccc4OC(F)(F)F)ccc2C)C3)cn1]

$^1$H NMR (400 MHz, DMSO-$d_6$) δ 9.62 (s, 1H), 9.31 (s, 1H), 8.78 (d, J=1.2 Hz, 1H), 8.46 (s, 1H), 8.24 (dd, J=1.6 Hz, J=8 Hz, 1H), 8.14 (s, 1H), 8.04 (dd, J=1.47 Hz, J=8.4 Hz, 1H), 7.53 (d, J=2 Hz, 1H), 7.34 (m, 2H), 7.24 (m, 2H), 7.16 (d, J=8.4 Hz, 1H), 7.08 (m, 1H), 4.7 (d, J=14.4 Hz, 1H), 4.48 (d, J=14.4 Hz, 1H), 3.32 (s, 3H), 2.39 (s, 3H), 2.08 (s, 3H).

Compound No. 4. Synthesis of 1-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-(trifluoromethyl)phenyl)urea

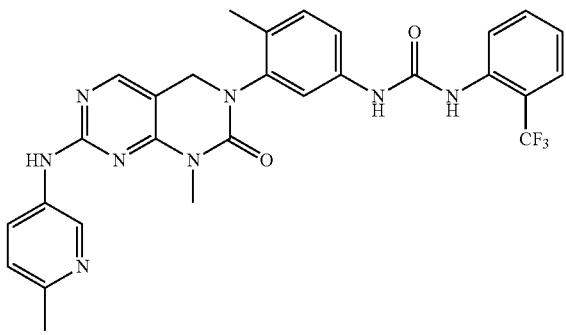 [SMILES: Cc1ccc(Nc2ncc3c(n2)N(C)C(=O)N(c2cc(NC(=O)Nc4ccccc4C(F)(F)F)ccc2C)C3)cn1]

¹H NMR (400 MHz, DMSO-d₆) δ 9.62 (s, 1H), 9.41 (s, 1H), 8.79 (d, J=2.8, 1H), 8.14 (s, 1H), 8.08 (s, 1H), 8.05 (dd, J=2.4 Hz, J=8 Hz, 1H), 7.94 (d, J=8.4 Hz, 1H), 7.67 (d, J=8 Hz, 1H), 7.63 (t, J=7.6 Hz, 1H), 7.54 (d, J=1.6 Hz, 1H), 7.25 (m, 3H), 7.17 (d, 8.4 Hz, 1H), 4.70 (d, J=14 Hz, 1H), 4.48 (d, J=14 Hz, 1H), 2.40 (s, 3H), 2.09 (s, 3H).

Compound No. 5. Synthesis of 1-(4-methyl-3-(1-methyl-7-((6-methylpyridin-3-yl)amino)-2-oxo-1,4-dihydropyrimido[4,5-d]pyrimidin-3(2H)-yl)phenyl)-3-(o-tolyl)urea

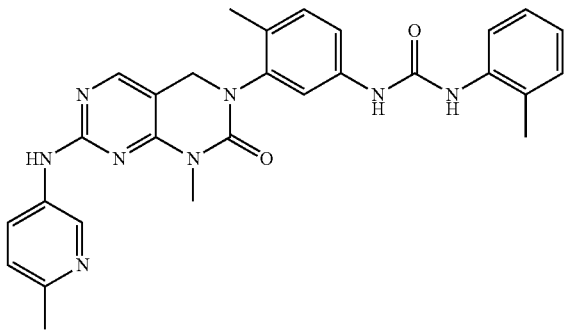 [SMILES: Cc1ccc(Nc2ncc3c(n2)N(C)C(=O)N(c2cc(NC(=O)Nc4ccccc4C)ccc2C)C3)cn1]

¹H NMR (400 MHz, DMSO-d₆) δ 9.62 (s, 1H), 9.04 (s, 1H), 8.78 (d, J=2.8 Hz, 1H), 8.14 (s, 1H), 8.04 (dd, J=2.8 Hz, J=8.4 Hz, 1H), 7.92 (s, 1H), 7.80 (d, J=8 Hz, 1H), 7.54 (d, J=2 Hz, 1H), 7.17 (m, 5H), 6.93 (td, J=1.2 Hz, J=7.4 Hz, 1H), 4.69 (d, J=14.4 Hz, 1H), 4.48 (d, J=14 Hz, 1H), 2.39 (s, 3H), 2.23 (s, 3H), 2.07 (s, 3H).

Compound No. 6. Synthesis of 1-(2,3-dichlorophenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea

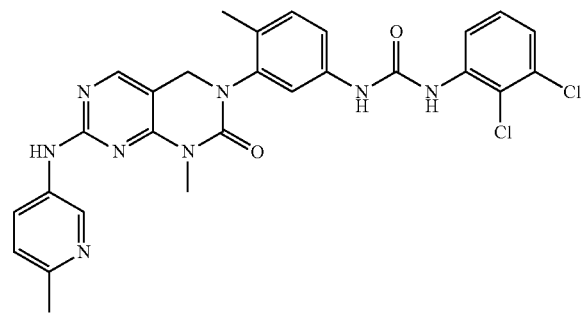 [SMILES: Cc1ccc(Nc2ncc3c(n2)N(C)C(=O)N(c2cc(NC(=O)Nc4cccc(Cl)c4Cl)ccc2C)C3)cn1]

¹H NMR (400 MHz, DMSO-d₆) δ 9.62 (s, 1H), 9.52 (s, 1H), 8.79 (d, J=2.4 Hz, 1H), 8.47 (s, 1H), 8.15 (m, 2H), 8.05 (dd, J=2.8 Hz, J=8 Hz, 1H), 7.55 (d, J=1.2 Hz, 1H), 7.27 (m, 4H), 7.16 (d, J=8.8 Hz, 1H), 4.70 (d, J=14 Hz, 1H), 4.48 (d, J=14.4 Hz, 1H), 2.40 (s, 3H), 2.09 (s, 3H).

Compound No. 7. Synthesis of 1-(4-methyl-3-(1-methyl-7-((6-methylpyridin-3-yl)amino)-2-oxo-1,4-dihydropyrimido[4,5-d]pyrimidin-3(2H)-yl)phenyl)-3-(3-(trifluoromethyl)phenyl)urea

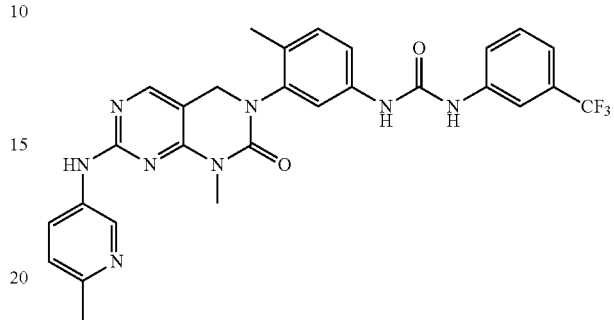

¹H NMR (400 MHz, DMSO-d₆) δ 9.63 (s, 1H), 9.06 (s, 1H), 8.82 (s, 1H), 8.78 (d, J=2.8 Hz, 1H), 8.14 (s, 1H), 8.04 (m, 2H), 7.53 (m, 3H), 7.29 (d, J=7.2 Hz, 1H), 7.22 (m, 2H), 7.17 (d, J=8.4 Hz, 1H), 4.70 (d, J=14.4 Hz, 1H), 4.48 (d, J=14 Hz, 1H), 2.39 (s, 3H), 2.08 (s, 3H).

Compound No. 8. Synthesis of 1-(3-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea

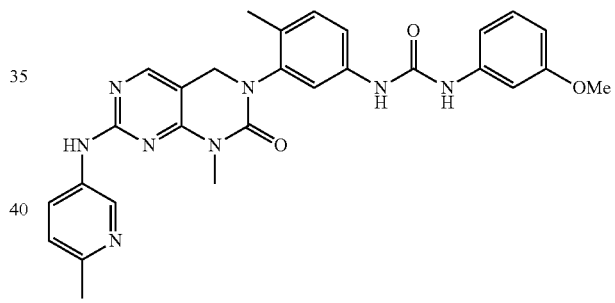

¹H NMR (400 MHz, DMSO-d₆) δ 8.75 (d, J=2 Hz, 1H), 8.09 (dd, J=2.8 Hz, J=9.8 Hz, 1H), 8.05 (s, 1H), 7.52 (s, 1H), 7.22 (m, 3H), 7.15 (m, 2H), 6.87 (qd, J=0.8 Hz, J=1.6 Hz, J=8.4 Hz, 1H), 6.57 (qd, J=0.8 Hz, J=2.8 Hz, J=8.2 Hz, 1H), 4.73 (dd, J=0.8, J=14.4 Hz, 1H), 4.51 (d, J=14.8 Hz, 1H), 3.75 (s, 3H), 3.41 (s, 3H), 2.47 (s, 3H), 2.16 (s, 3H).

Compound No. 9. Synthesis of 1-(4-chloro-3-(trifluoromethyl)phenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea

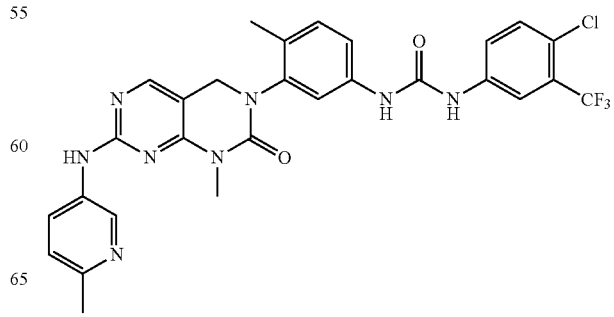

¹H NMR (400 MHz, DMSO-d₆) δ 9.62 (s, 1H), 9.20 (s, 1H), 8.89 (s, 1H), 8.77 (d, J=2.4 Hz, 1H) 8.13 (s, 1H), 8.11 (s, 1H), 8.04 (dd, J=2.8 Hz, J=8.6 Hz, 1H), 7.60 (s, 1H), 7.53 (s, 1H), 7.21 (m, 3H), 4.69 (d, J=14 Hz, 1H), 4.47 (d, J=14.4 Hz, 1H), 3.31 (s, 1H), 2.39 (s, 1H), 2.07 (s, 1H).

Compound No. 10. Synthesis of 1-(4-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 10)

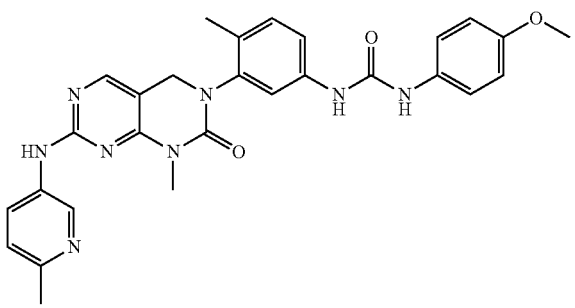 [SMILES: COc1ccc(NC(=O)Nc2ccc(C)c(N3Cc4cnc(Nc5ccc(C)nc5)nc4N(C)C3=O)c2)cc1]

¹H NMR (400 MHz, DMSO-d₆) δ 9.62 (s, 1H), 8.79 (d, J=2.9 Hz, 1H), 8.59 (s, 1H), 8.48 (s, 1H), 8.14 (s, 1H), 8.05 (dd, J=2.4 Hz, J=8 Hz, 1H), 7.52 (d, J=2 Hz, 1H), 7.35 (m, 2H), 7.21 (m, 3H), 6.86 (m, 2H), 4.69 (d, J=14.4 Hz, 1H), 4.48 (d, J=14 Hz, 1H), 3.71 (s, 3H), 3.32 (s, 3H), 2.40 (s, 3H), 2.08 (s, 3H).

Representative Synthetic Example 2

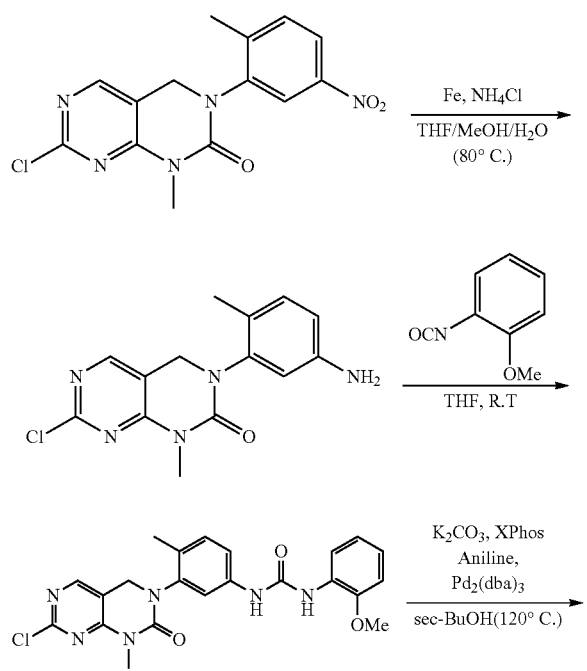

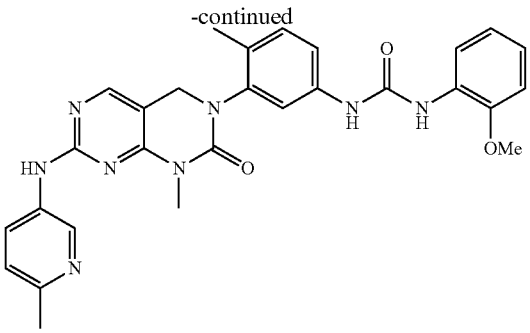

Step 2-1: 3-(5-Amino-2-methylphenyl)-7-chloro-1-methyl-3,4-dihydropyrimido[4,5-d]pyrimidin-2(1H)-one 7-Chloro-1-methyl-3-(2-methyl-5-nitrophenyl)-3,4-dihydropyrimido[4,5-d]pyrimidin-2(1H)-one (1.4 g, 4.2 mmol) and ammonium chloride (4.5 g, 84 mmol) were added to a mixed solution of THF/methanol/water (4:2:1, 17.5 mL), then iron powder (2.3 g, 42 mmol) was added, and stirred at 80° C. for 2 hours. When the reaction was completed, the reaction mixture was cooled to room temperature and filtered using a celite pad. The filtrate was extracted with dichloromethane and water. The combined organic layers were dried over anhydrous magnesium sulfate and concentrated to obtain the desired compound (1.1 g, 87.3%) as a pale yellow solid.
¹H NMR (400 MHz, DMSO-d₆) δ 8.29 (s, 1H), 6.92 (m, 1H), 6.49 (m, 2H), 5.04 (s, 2H), 4.74 (d, J=0.8 Hz, 1H), 4.70 (d, J=0.8 Hz, 1H), 3.26 (s, 3H), 1.95 (s, 3H).

Step 2-2: 1-(3-(7-Chloro-1-methyl-2-oxo-1,4-dihydropyrimido[4,5-d]pyrimidin-3(2H)-yl)-4-methylphenyl-3-(2-methoxyphenyl)urea 3-(5-Amino-2-methylphenyl)-7-chloro-1-methyl-3,4-dihydropyrimido[4,5-d]pyrimidin-2(1H)-one (100 mg, 0.33 mmol) was dissolved in THF (6.6 mL), then 2-methoxyphenyl isocyanate (0.06 mL, 0.43 mmol) was added, and the mixture was stirred at room temperature. After 1 hour, when the reaction was completed, the reaction mixture was extracted with dichloromethane and water, and the combined organic layers were dried over anhydrous magnesium sulfate and concentrated. The residue was purified by column chromatography to obtain the desired compound (127.1 mg, 85%) as a white solid.
¹H NMR (400 MHz, DMSO-d₆) δ 9.35 (s, 1H), 8.31 (s, 1H), 8.21 (s, 1H), 8.10 (dd, J=1.6 Hz, J=8 Hz, 1H), 7.56 (s, 1H), 7.20 (m, 2H), 7.00 (dd, J=1.6 Hz, J=8 Hz, 1H), 6.93 (td, J=1.6 Hz, J=8 Hz, 1H), 6.87 (td, J=1.2 Hz, J=7.6 Hz, 1H), 4.81 (d, J=15.6 Hz, 1H), 4.61 (d, J=15.6 Hz, 1H), 3.86 (s, 3H), 3.27 (s, 3H), 2.07 (s, 3H).

Step 3: 1-(3-(7-((4-(4-Ethylpiperazin-1-yl)phenyl)amino)-1-methyl-2-oxo-1,4-dihydropyrimido[4,5-d]pyrimidin-3(2H)-yl)-4-methylphenyl)-3-(2-methoxyphenyl)urea (Compound No. 11)

1-(3-(7-Chloro-1-methyl-2-oxo-1,4-dihydropyrimido[4,5-d]pyrimidin-3(2H)-yl)-4-methylphenyl)-3-(2-methoxyphenyl)urea (80 mg, 0.17 mmol) was dissolved in 2-butanol (0.85 mL). 4-(4-Ethylpiperazin-1-yl)aniline (38 mg, 0.19 mmol) and potassium carbonate (70.5 mg, 0.51 mmol) were added, the reaction vessel was transferred into an oil bath heated to 110° C., and Pd₂(dba)₃ (31 mg, 0.03 mmol) and Xphos (16.2 mg, 0.03 mmol) were added and stirred for 90 minutes. Then, when the reaction was completed, the reaction mixture was filtered using a celite pad and concentrated. The residue was purified by MPLC to obtain the desired compound (73.2 mg, 66.8%) as a white solid.

Based on the method of Representative Synthesis Example 2, the compounds represented by Compound Nos. 11 to 18 were synthesized.

Compound No. 11. Synthesis of 1-(3-(7-((4-(4-ethylpiperazin-1-yl)phenyl)amino)-1-methyl-2-oxo-1,4-dihydropyrimido[4,5-d]pyrimidin-3(2H)-yl)-4-methylphenyl)-3-(2-methoxyphenyl)urea

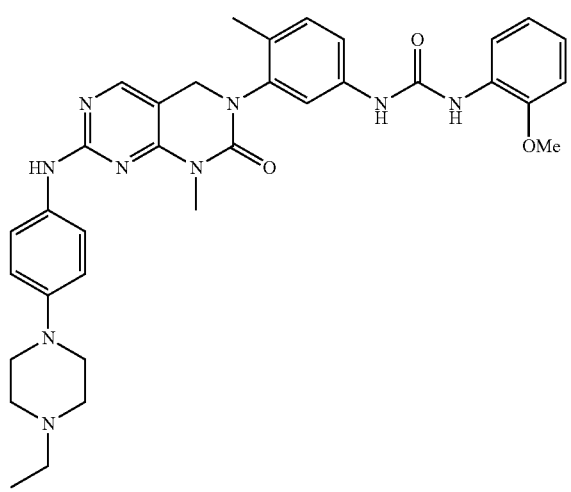 [SMILES: CCN1CCN(c2ccc(Nc3ncc4c(n3)N(C)C(=O)N(c3cc(NC(=O)Nc5ccccc5OC)ccc3C)C4)cc2)CC1]

¹H NMR (400 MHz, DMSO-d₆) δ 9.33 (s, 1H), 9.28 (s, 1H), 8.21 (s, 1H), 8.10 (dd, J=1.6 Hz, J=8 Hz, 1H), 8.07 (s, 1H), 7.58 (d, J=8.8 Hz, 2H), 7.58 (s, 1H), 7.52 (d, J=1.6 Hz, 1H), 7.20 (m, 2H), 7.00 (dd, J=1.6 Hz, J=8 Hz, 1H), 6.93 (td, J=1.6 Hz, J=8 Hz, 1H), 6.86 (m, 3H), 4.66 (d, J=14 Hz, 1H), 4.44 (d, J=14.4 Hz, 1H), 3.86 (s, 3H), 3.05 (t, J=4 Hz, 4H), 2.35 (q, J=7.2 Hz, 2H), 2.07 (d, J=2 Hz, 3H), 1.02 (t, J=7.2 Hz, 3H).

Compound No. 12. Synthesis of 1-(2-methoxyphenyl)-3-(4-methyl-3-(1-methyl-7-((1-methy-1H-pyrazol-4-yl)amino)-2-oxo-1,4-dihydropyrimido[4,5-d]pyrimidin-3(2H)-yl)phenyl)urea

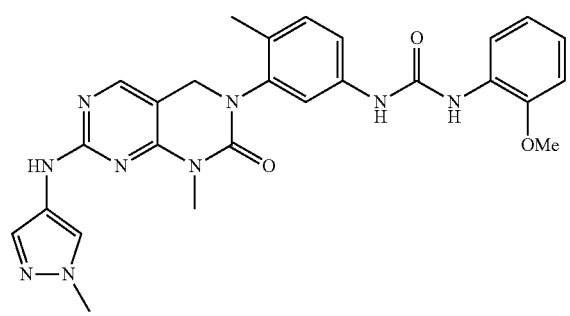 [SMILES: COc1ccccc1NC(=O)Nc1ccc(C)c(N2Cc3cnc(Nc4cnn(C)c4)nc3N(C)C2=O)c1]

¹H NMR (400 MHz, DMSO-d₆) δ 9.40 (s, 1H), 9.35 (s, 1H), 8.22 (s, 1H), 8.11 (dd, J=1.6 Hz, J=8 Hz, 1H), 8.08 (s, 1H), 7.54 (d, J=1.2 Hz, 1H), 7.50 (s, 1H), 7.21 (m, 2H), 7.01 (dd, J=1.2 Hz, J=8 Hz, 1H), 6.91 (m, 2H), 4.67 (d, J=14 Hz, 1H), 4.45 (d, J=14 Hz, 1H), 3.88 (s, 3H), 3.81 (s, 3H), 2.08 (s, 3H).

Compound No. 13. Synthesis of 1-(3-(7-((6-(4-acetylpiperazin-1-yl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea

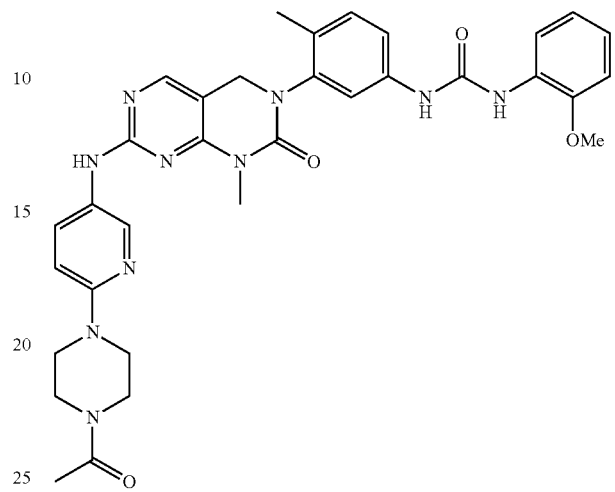

¹H NMR (400 MHz, DMSO-d₆) δ 9.30 (d, J=8 Hz, 2H), 8.47 (d, J=2.4 Hz, 1H), 8.19 (s, 1H), 8.1 (dd, J=1.6 Hz, J=8 Hz, 1H), 8.07 (s, 1H), 7.91 (dd, J=2.8 Hz, J=9.2 Hz, 1H), 7.52 (s, 1H), 7.20 (m, 2H), 7.00 (dd, J=1.6 Hz, J=8.4 Hz, 1H), 6.93 (td, J=1.6 Hz, J=7.2 Hz, 1H), 6.88 (m, 2H), 4.66 (d, J=14.4 Hz, 1H), 4.45 (d, J=14.4 Hz, 1H), 3.86 (s, 3H), 3.53 (m, 4H), 3.45 (m, 2H), 3.38 (m, 2H), 3.30 (s, 3H), 2.07 (s, 3H), 2.03 (s, 3H).

Compound No. 14. Synthesis of 1-(3-(7-((6-(4-ethylpiperazin-1-carbonyl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea

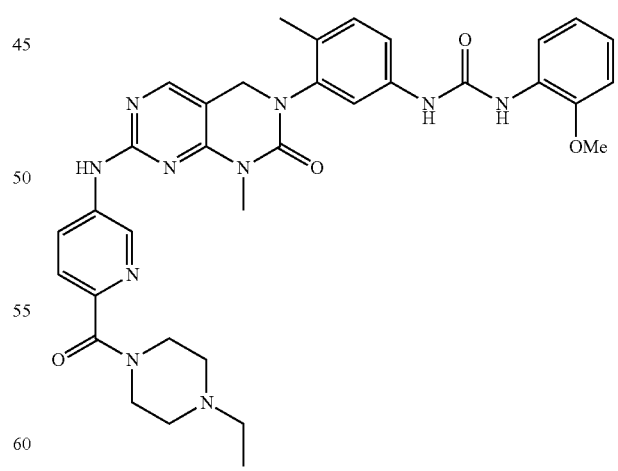

¹H NMR (400 MHz, DMSO-d₆) δ 9.99 (s, 1H), 9.34 (s, 1H), 8.90 (d, J=2.4 Hz, 1H), 8.34 (dd, J=2.8 Hz, J=8.8 Hz, 1H), 8.21 (s, 1H), 8.20 (s, 1H), 8.11 (dd, J=1.6 Hz, J=8 Hz, 1H), 7.59 (s, 1H), 7.56 (d, J=3.6 Hz, 1H), 7.21 (m, 2H), 7.01 (dd, J=1.6 Hz, J=8 Hz, 1H), 6.94 (td, J=1.6 Hz, J=7.6 Hz,

1H), 6.87 (td, J=1.2 Hz, J=8 Hz, 1H), 4.73 (d, J=14.4 Hz, 1H), 4.52 (d, J=14.4 Hz, 1H), 3.87 (s, 3H), 3.62 (s, 2H), 3.55 (s, 2H), 3.36 (s, 3H), 2.41 (s, 2H), 2.35 (q, J=7.2 Hz, 4H), 2.08 (s, 3H), 1.00 (t, J=7.2 Hz, 3H).

Compound No. 15. Synthesis of 5-((6-(5-(3-(2-methoxyphenyl)ureido)-2-methyl phenyl)-8-methyl-7-oxo-5,6,7,8-tetrahydropyrimido[4,5-d]pyrimidin-2-yl)amino-N-methylpicolinamide

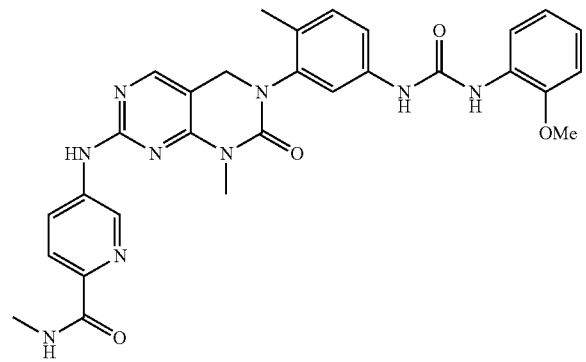 [SMILES: CNC(=O)c1ccc(Nc2ncc3c(n2)N(C)C(=O)N(c2cc(NC(=O)Nc4ccccc4OC)ccc2C)C3)cn1]

$^1$H NMR (400 MHz, DMSO-d$_6$) δ 10.10 (s, 1H), 9.37 (s, 1H), 9.02 (d, J=2 Hz, 1H), 8.58 (d, J=4 Hz, 1H), 8.34 (dd, J=2.4 Hz, J=8.8 Hz, 1H), 8.23 (d, J=6.4 Hz, 2H), 8.1 (dd, J=1.6 Hz, J=8 Hz, 1H), 7.97 (d, J=8.8 Hz, 1H), 7.56 (s, 1H), 7.21 (s, 2H), 7.01 (d, J=6.8 Hz, 1H), 6.94 (td, J=2 Hz, J=8 Hz, 1H), 6.87 (m, 1H), 4.74 (d, J=14.4 Hz, 1H), 4.53 (d, J=14.4 Hz, 1H), 3.87 (s, 3H), 3.37 (s, 3H), 2.80 (d, J=4.8 Hz, 3H), 2.08 (s, 3H).

Compound No. 16. Synthesis of N-cyclopropyl-5-((6-(5-(3-(2-methoxyphenyl)ureido)-2-methylphenyl)-8-methyl-7-oxo-5,6,7,8-tetrahydropyrimido[4,5-d]pyrimidin-2-yl)amino)picolinamide

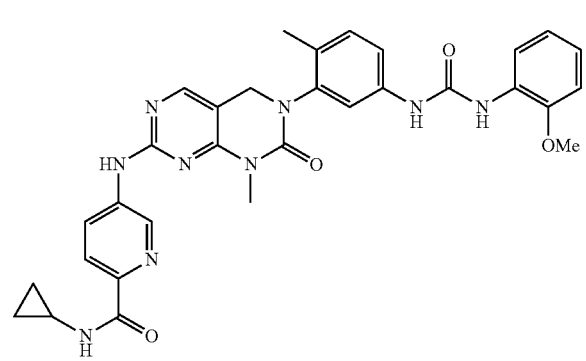 [SMILES: COc1ccccc1NC(=O)Nc1ccc(C)c(N2Cc3cnc(Nc4ccc(C(=O)NC5CC5)nc4)nc3N(C)C2=O)c1]

$^1$H NMR (400 MHz, DMSO-d$_6$) δ 10.10 (s, 1H), 9.37 (s, 1H), 9.01 (d, J=2.4 Hz, 1H), 8.53 (d, J=4.8 Hz, 1H) 8.34 (dd, J=2.4 Hz, J=8.4 Hz, 1H), 8.23 (s, 1H), 8.22 (s, 1H), 8.11 (dd, J=1.6 Hz, J=8 Hz, 1H), 7.97 (d, J=8.8 Hz, 1H), 7.56 (s, 1H), 7.21 (s, 2H), 7.01 (dd, J=1.6 Hz, J=8 Hz, 1H), 6.94 (td, J=1.6 Hz, J=7.2 Hz, 1H), 6.87 (m, 1H), 4.74 (d, J=14 Hz, 1H), 4.52 (d, J=14 Hz, 1H), 0.3.87 (s, 3H), 3.32 (s, 3H), 2.88 (m, 1H), 2.08 (s, 3H), 0.67 (m, 4H).

Compound No. 17. Synthesis of 1-(3-(7-((6-(4-ethylpiperazin-1-yl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea

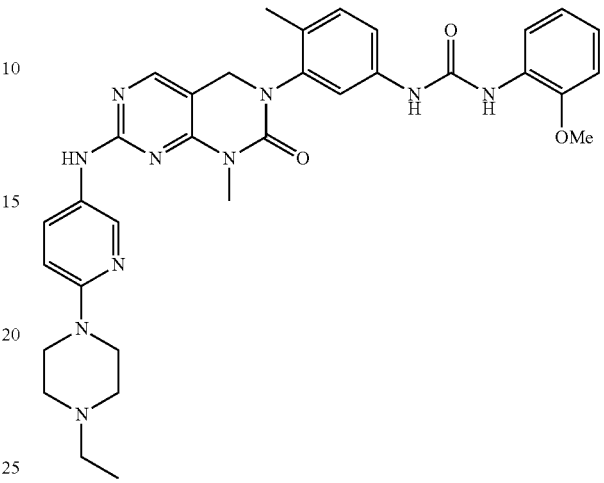

$^1$H NMR (400 MHz, DMSO-d$_6$) δ 9.35 (s, 1H), 9.31 (s, 1H), 8.46 (d, J=2.8 Hz, 1H), 8.23 (s, 1H), 8.12 (dd, J=1.6 Hz, J=8 Hz, 1H), 8.08 (s, 1H), 7.89 (dd, J=2.4 Hz, J=8.8 Hz, 1H), 7.54 (s, 1H), 7.21 (m, 2H), 7.02 (dd, J=1.2 Hz, J=8 Hz, 1H), 6.94 (td, J=1.2 Hz, J=8 Hz, 1H), 6.88 (td, J=1.2 Hz, J=8 Hz, 1H), 6.82 (d, J=9.2 Hz, 1H), 4.68 (d, J=14 Hz, 1H), 4.46 (d, J=14 Hz, 1H), 3.88 (s, 3H), 3.39 (t, 4.8 Hz, 4H), 3.31 (s, 3H), 2.45 (t, 4.8 Hz, 4H), 2.36 (q, J=7.2 Hz, 2H), 2.08 (s, 3H), 1.04 (t, J=7.2 Hz, 3H).

Compound No. 18. Synthesis of 1-(5-((6-(5-(3-(2-methoxyphenyl)ureido)-2-methylphenyl)-8-methyl-7-oxo-5,6,7,8-tetrahydropyrimido[4,5-d]pyrimidin-2-yl)amino)pyridin-2-yl)piperidin-4-carboxamide

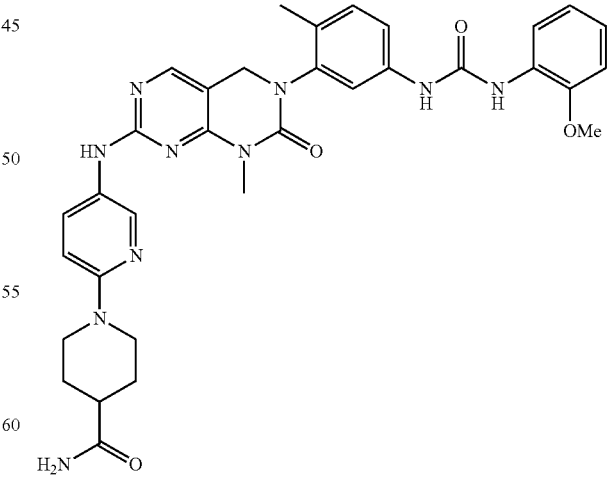

$^1$H NMR (400 MHz, DMSO-d$_6$) δ 9.33 (s, 1H), 9.27 (s, 1H), 8.43 (d, J=2.8 Hz, 1H), 8.21 (s, 1H), 8.11 (dd, J=1.6 Hz, J=8 Hz, 1H), 8.07 (s, 1H), 7.86 (dd, J=2.4 Hz, J=8.8 Hz, 1H), 7.52 (d, J=1.6 Hz, 1H), 7.26 (s, 1H), 7.21 (m, 2H), 7.01 (dd,

J=1.6 Hz, J=8 Hz, 1H), 6.94 (td, J=1.6 Hz, J=7.6 Hz, 1H), 6.87 (td, J=1.2 Hz, J=8 Hz, 1H), 6.83 (d, J=9.2 Hz, 1H), 6.75 (s, 1H), 4.67 (d, J=14 Hz, 1H), 4.45 (d, J=14 Hz, 1H), 4.20 (d, J=13.2 Hz, 2H), 3.87 (s, 3H), 3.30 (s, 3H), 2.74 (td, J=2.4 Hz, J=12.4 Hz, 2H), 2.31 (m, 1H), 2.27 (s, 2H), 2.08 (s, 2H), 1.74 (d, J=10.4 Hz, 2H), 1.50 (qd, J=4 Hz, J=12.4 Hz, J=24.4 Hz, 2H).

Test Examples

Test Example 1. Measurement of Kinase Inhibitory Activity

In order to measure the protein kinase inhibitory activity (% inhibition) of the compounds of the present invention, biochemical assays were performed on the full kinase panel listed in the following Table 1.

As an test compound, 1-(3-(7-((6-(4-ethylpiperazine-1-carbonyl)pyridin-3-yl)amino)-1-methyl-2-oxo-1,4-dihydro-pyrimido[4,5-d]pyrimidin-3(2H)-yl)-4-methylphenyl)-3-(2-methoxyphenyl)urea (Compound No. 14) was used. The kinase inhibitory efficacy was measured upon treatment with a 1 μM single concentration of the test compound to calculate % residual enzyme activity value. The kinases for which calculated % residual enzyme activity value is 30% or less (that is, when inhibited by 70% or more) are exhibited as follows.

<Kinases Exhibiting Inhibition of 70% or More>
ABL1, FGFR2, TAOK2/TAO1, EPHA5, EPHB2, EPHB3, RET, LYN B, EPHA2, FRK/PTK5, EPHA8, LCK, EPHB4, FYN, KHS/MAP4K5, DDR1, EPHA3, P38a/MAPK14, EPHA4, FMS, EPHB1, HCK, FGFR1, ABL2/ARG, EPHA6, c-Src, ACK1, FLT4NEGFR3, ERBB4/HER4, DDR2, KDRNEGFR2, LYN, ZAK/MLTK, YES/YES1, BLK, FGR, MLCK2/MYLK2, TAOK1, BMX/ETK, BTK, EPHA1, JAK1, P38b/MAPK11, TIE2/TEK, FLT1NEGFR1, TXK, SRMS, RAF1, SIK1, MLK3/MAP3K11, PEAK1, TRKA, EPHA7, GLK/MAP4K3, MLK2/MAP3K10, TEC, CSK, TRKC, FES/FPS, SIK2, FGFR3, BRK, YSK4/MAP3K19, ARAF, PDGFRb, TNK1, GCK/MAP4K2, PDGFRa, TNIK, TAK1, ERBB2/HER2, LIMK1, HIPK4, FER, EGFR, JAK2, HPK1/MAP4K1, TRKB, RIPK3, LOK/STK10, LIMK2, MLK1/MAP3K9, BRAF, MEKK3, MEK5, STK32B/YANK2, FGFR4, MEKK2, SLK/STK2, FLT3, PKAcg, TAOK3/JIK, TYRO3/SKY, SIK3, IR, LRRK2, PYK2, NEK11, p70S6K/RPS6KB1, LATS2.

Referring to the FIGURE, there is accompanied a schematic representation illustrating the measurement results for the inhibitory efficacy of the compound of the present invention against 100 types of kinases.

Test Example 2: GCK and ACK1 Kinase Inhibitory Activity $GI_{50}$ values were calculated by measuring the inhibitory efficacy of the compounds of the present invention against both GCK and ACK1 kinases. The calculated $GI_{50}$ values are listed in the following Table 1.

TABLE 1

| Test Compound | Kinase inhibitory efficacy, $GI_{50}$ | |
|---|---|---|
| | GCK | ACK1 |
| Compound No. 1 | B | A |
| Compound No. 2 | C | A |
| Compound No. 3 | D | A |
| Compound No. 4 | D | A |

TABLE 1-continued

| Test Compound | Kinase inhibitory efficacy, $GI_{50}$ | |
|---|---|---|
| | GCK | ACK1 |
| Compound No. 5 | C | A |
| Compound No. 6 | C | A |
| Compound No. 7 | C | A |
| Compound No. 8 | B | A |
| Compound No. 9 | C | B |
| Compound No. 10 | B | B |
| Compound No. 11 | A | A |
| Compound No. 12 | A | A |
| Compound No. 13 | A | A |
| Compound No. 14 | A | A |
| Compound No. 15 | C | A |
| Compound No. 16 | C | A |
| Compound No. 17 | A | A |
| Compound No. 18 | A | B |

[Classification of $GI_{50}$]
A: less than 0.03 μM,
B: 0.03 μM to 0.1 μM,
C: 0.1 μM to 0.3 μM,
D: 0.3 μM or more Test Example 3. Proliferation Inhibitory Activity $GI_{50}$ values were calculated by measuring the proliferation inhibitory efficacy of the compounds of the present invention on mt-NRAS (G12D) Ba/F3, U937 (wt-NRAS) and OCI-AML3 (mt-NRAS) cell lines. The calculated $GI_{50}$ values are listed in the following Table 2.

TABLE 2

| Test Compound | Proliferation inhibitory efficacy ($GI_{50}$, μM) | | |
|---|---|---|---|
| | OCI-AML3 (N-Ras Q61L) | U937 (N-Ras WT) | Ba/F3 (N-Ras G12D) |
| Compound No. 1 | A | D | A |
| Compound No. 2 | B | D | B |
| Compound No. 3 | B | D | C |
| Compound No. 4 | A | D | B |
| Compound No. 5 | B | D | B |
| Compound No. 6 | A | D | B |
| Compound No. 7 | B | D | A |
| Compound No. 8 | B | D | A |
| Compound No. 9 | A | D | B |
| Compound No. 10 | A | D | A |
| Compound No. 11 | A | B | A |
| Compound No. 12 | A | D | A |
| Compound No. 13 | A | D | A |
| Compound No. 14 | A | D | B |
| Compound No. 15 | A | D | A |
| Compound No. 16 | A | D | A |
| Compound No. 17 | A | B | A |
| Compound No. 18 | A | D | A |

[Classification of $GI_{50}$]
A: less than 0.5 μM,
B: 0.5 μM to 3.0 μM,
C: 3.0 μM to 5.0 μM,
D: 5.0 μM or more According to the results listed in Table 2, it can be seen that the compounds of the present invention exhibit a proliferation inhibitory activity, which is remarkable in terms of effects, against the human acute myelogenous leukemia cell line (OCI-AML3) having an NRAS mutant gene while exhibiting a low inhibitory activity against the NRAS-wild type (U937). Accordingly, the compounds of the present invention are particularly effective as a therapeutic agent for acute myelogenous leukemia (AML).

Formulation Examples

On the other hand, the novel compound represented by the above Formula 1 according to the present invention can be formulated into various forms depending on the purpose. The following illustrates some formulation methods in which the compound of the above Formula 1 according to the present invention is included as an active ingredient, but the present invention is not limited thereto.

Formulation Example 1: Tablets (Direct Compression)

After 5.0 mg of the active ingredient was sieved, 14.1 mg of lactose, 0.8 mg of Crospovidone USNF and 0.1 mg of magnesium stearate were mixed and compressed into tablets.

Formulation Example 2: Tablets (Wet Assembly)

After 5.0 mg of the active ingredient was sieved, 16.0 mg of lactose and 4.0 mg of starch were mixed. 0.3 mg of Polysorbate 80 was dissolved in pure water, and an appropriate amount of this solution was added, followed by atomization. After drying, the particulates were sieved and mixed with 2.7 mg of colloidal silicon dioxide and 2.0 mg of magnesium stearate. The particulates were compressed into tablets.

Formulation Example 3: Powders and Capsules

After 5.0 mg of the active ingredient was sieved, 14.8 mg of lactose, 10.0 mg of polyvinyl pyrrolidone and 0.2 mg of magnesium stearate were mixed together. The mixture was filled into a hard No. 5 gelatin capsule with a proper apparatus.

Formulation Example 4: Injections

Injections were prepared by including 100 mg of the active ingredient, and further including 180 mg of mannitol, 26 mg of $Na_2HPO_4 \cdot 12H_2O$ and 2974 mg of distilled water.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A compound represented by the following Formula 1, or a pharmaceutically acceptable salt thereof:

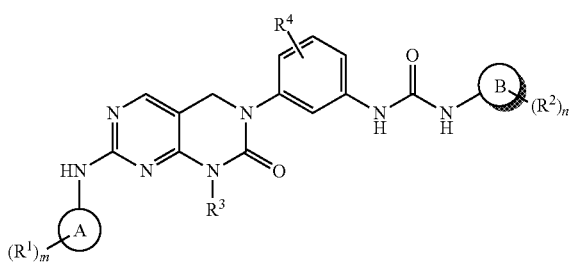

wherein in the above Formula 1,
A represents a phenyl group or a pyridinyl group,
B represents a phenyl group,
$R^1$ and $R^2$ each represents a halogen atom, an oxo group (=O), a $C_1$-$C_6$ alkyl group, a $C_1$-$C_6$ haloalkyl group, —O—($C_1$-$C_6$ alkyl), —O—($C_1$-$C_6$ haloalkyl), —C(O)—($C_1$-$C_6$ alkyl), —C(O)—O—($C_1$-$C_6$ alkyl), —O—C(O)—($C_1$-$C_6$ alkyl), —$NR^5R^6$, —C(O)—$NR^5R^6$, or —O—($C_1$-$C_6$ alkyl)-$NR^5R^6$,
$R^3$ represents a hydrogen atom, a $C_1$-$C_6$ alkyl group, —O—($C_1$-$C_6$ alkyl), or —C(O)—($C_1$-$C_6$ alkyl),
$R^4$ represents a hydrogen atom, a $C_1$-$C_6$ alkyl group, or —O—($C_1$-$C_6$ alkyl);
$R^5$ and $R^6$ each represents a hydrogen atom or a $C_1$-$C_6$ alkyl group, or $R^5$ and $R^6$ may be bonded to each other to form a 5- to 6-membered heterocyclic group including 1 to 2 hetero atoms selected from nitrogen (N) and oxygen (O) atoms, wherein the heterocyclic group may be optionally substituted by a hydroxyl group, $C_1$-$C_6$ alkyl, —($C_1$-$C_6$ hydroxyalkyl), —O—($C_1$-$C_6$ alkyl), —C(O)—($C_1$-$C_6$ alkyl), or —C(O)$NH_2$, and
m and n are each an integer of 0 to 3.

2. The compound according to claim 1, wherein:
$R^1$ represents a $C_1$-$C_6$ alkyl group, —C(O)—($C_1$-$C_6$ alkyl), or —$NR^5R^6$, —C(O)—$NR^5R^6$,
$R^2$ represents a halogen atom, a $C_1$-$C_6$ alkyl group, a $C_1$-$C_6$ haloalkyl group, —O—($C_1$-$C_6$ alkyl), or —O—($C_1$-$C_6$ haloalkyl),
$R^3$ represents a hydrogen atom or a $C_1$-$C_6$ alkyl group,
$R^4$ represents a hydrogen atom or a $C_1$-$C_6$ alkyl group,
$R^5$ and $R^6$ each represents a hydrogen atom or a $C_1$-$C_6$ alkyl group, or $R^5$ and $R^6$ may be bonded to each other to form a heterocyclic group selected from piperidine, piperazinyl and morpholyl, wherein the heterocyclic group may be optionally substituted by a $C_1$-$C_6$ alkyl group, —C(O)—($C_1$-$C_6$ alkyl) or —C(O)$NH_2$, and
m and n each represents an integer of 0, 1 or 2.

3. The compound according to claim 1, wherein:
$R^1$ represents a methyl group, an ethyl group, a propyl group, a piperidinyl group, a 4-(carbamoyl)piperidinyl group, a piperazinyl group, a 4-(ethyl)piperazinyl group, a 4-(acetyl)piperazinyl group, a 4-(carbamoyl)piperazinyl group, —C(O)$NHCH_3$, —C(O)NH-cyclopropane, —C(O)-piperidine, —C(O)-piperazine, or —C(O)-4-(ethyl)piperazine, and
m represents an integer of 0, 1 or 2.

4. The compound according to claim 1, wherein:
$R^2$ represents chloro, fluoro, a methyl group, a methoxy group, an ethyl group, an ethoxy group, a trifluoromethyl group, or a trifluoromethoxy group, and
m represents an integer of 0, 1 or 2.

5. A compound represented by the following compound number or a Pharmaceutically acceptable salt thereof:
1-(2-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 1);
1-(4-methyl-3-(1-methyl-7-((6-methylpyridin-3-yl)amino)-2-oxo-1,4-dihydropyrimido[4,5-d]pyrimidin-3(2H)-yl)phenyl)-3-phenylurea (Compound No. 2);
1-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-(trifluoromethoxy)phenyl)urea (Compound No. 3);
1-(4-methyl-3-(1-methyl-7-((6-methylpyridin-3-yl)amino)-2-oxo-1,4-dihydropyrimido[4,5-d]pyrimidin-3(2H)-yl)phenyl)-3-(2-(trifluoromethyl)phenyl)urea (Compound No. 4);

1-(4-methyl-3-(1-methyl-7-((6-methylpyridin-3-yl)amino)-2-oxo-1,4-dihydropyrimido[4,5-d]pyrimidin-3(2H)-yl)phenyl)-3-(o-tolyl)urea (Compound No. 5);

1-(2,3-dichlorophenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 6);

1-(4-methyl-3-(1-methyl-7-((6-methylpyridin-3-yl)amino)-2-oxo-1,4-dihydropyrimido[4,5-d]pyrimidin-3(2H)-yl)phenyl)-3-(3-(trifluoromethyl)phenyl)urea (Compound No. 7);

1-(3-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 8);

1-(4-chloro-3-(trifluoromethyl)phenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 9);

1-(4-methoxyphenyl)-3-(4-methyl-3-(1-methyl-7-((6-methylpyridin-3-yl)amino)-2-oxo-1,4-dihydropyrimido[4,5-d]pyrimidin-3(2H)-yl)phenyl)urea (Compound No. 10);

1-(3-(7-((4-(4-ethylpiperazin-1-yl)phenyl)amino)-1-methyl-2-oxo-1,4-dihydropyrimido[4,5-d]pyrimidin-3(2H)-yl)-4-methylphenyl)-3-(2-methoxyphenyl)urea (Compound No. 11);

1-(2-methoxyphenyl)-3-(4-methyl-3-(1-methyl-7-((1-methy-1H-pyrazol-4-yl)amino)-2-oxo-1,4-dihydropyrimido[4,5-d]pyrimidin-3(2H)-yl)phenyl)urea (Compound No. 12);

1-(3-(7-((6-(4-acetylpiperazin-1-yl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea (Compound No. 13);

1-(3-(7-((6-(4-ethylpiperazin-1-carbonyl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea (Compound No. 14);

5-((6-(5-(3-(2-methoxyphenyl)ureido)-2-methylphenyl)-8-methyl-7-oxo-5,6,7,8-tetrahydropyrimido[4,5-d]pyrimidin-2-yl)amino-N-methylpicolinamide (Compound No. 15);

N-cyclopropyl-5-((6-(5-(3-(2-methoxyphenyl)ureido)-2-methylphenyl)-8-methyl-7-oxo-5,6,7,8-tetrahydropyrimido[4,5-d]pyrimidin-2-yl)amino)picolinamide (Compound No. 16);

1-(3-(7-((6-(4-ethylpiperazin-1-yl)pyridin-3-yl)amino)-1-methyl-2-oxo-1,4-dihydropyrimido[4,5-d]pyrimidin-3(2H)-yl)-4-methylphenyl)-3-(2-methoxyphenyl)urea (Compound No. 17); or 1-(5-((6-(5-(3-(2-methoxyphenyl)ureido)-2-methylphenyl)-8-methyl-7-oxo-5,6,7,8-tetrahydropyrimido[4,5-d]pyrimidin-2-yl)amino)pyridin-2-yl)piperidin-4-carboxamide (Compound No. 18).

6. A method for treatment or alleviation of a cancer disease caused by mutation of NRAS, wherein the method comprises administering an effective amount of the compound of claim 1 or a pharmaceutically acceptable salt thereof to a subject in need of said treatment or alleviation.

7. The method according to claim 6, wherein the cancerous disease is selected from the group consisting of melanoma, colorectal cancer, thyroid cancer, and hematologic malignancy.

8. The method according to claim 6, wherein the cancerous disease is acute myelogenous leukemia (AML).

9. A method for treatment or alleviation of a cancerous disease caused by mutations of NRAS, wherein the method comprises administering an effective amount of the compound of claim 5, or a pharmaceutically acceptable salt thereof, to a subject in need of said treatment or alleviation.

10. The method according to claim 9, wherein the cancerous disease is selected from the group consisting of melanoma, colorectal cancer, thyroid cancer, and hematologic malignancy.

11. The method according to claim 9, wherein the cancerous disease is acute myelogenous leukemia (AML).

\* \* \* \* \*